United States Patent [19]

Hara et al.

[11] Patent Number: 5,432,160
[45] Date of Patent: Jul. 11, 1995

[54] NUTRIENT COMPOSITION

[75] Inventors: Takahiro Hara, Tsuchiura; Yoshiharu Yokoo, Ushiku, both of Japan

[73] Assignee: Kyowa Hakko Kohyo Co., Ltd., Tokyo, Japan

[21] Appl. No.: 295,842

[22] PCT Filed: Jan. 26, 1994

[86] PCT No.: PCT/JP94/00101
§ 371 Date: Aug. 29, 1994
§ 102(e) Date: Aug. 29, 1994

[87] PCT Pub. No.: WO94/16688
PCT Pub. Date: Aug. 4, 1994

[30] Foreign Application Priority Data

Jan. 29, 1993 [JP] Japan .................. 5-014240

[51] Int. Cl.$^6$ .................. A61K 38/00; C07K 5/06
[52] U.S. Cl. .................. 514/19; 426/656
[58] Field of Search .................. 514/19; 426/656

[56] References Cited

U.S. PATENT DOCUMENTS

| 4,024,286 | 5/1977 | Cornelius et al. | 426/62 |
| 4,340,592 | 7/1982 | Adibi | 514/18 |
| 5,034,377 | 7/1991 | Adibi et al. | 514/18 |
| 5,102,871 | 4/1992 | Furukawa et al. | 514/11 |
| 5,134,125 | 7/1992 | Hara et al. | 514/19 |

FOREIGN PATENT DOCUMENTS 9209277 6/1992 WIPO .

*Primary Examiner*—Marianne M. Cintins
*Assistant Examiner*—K. Weddington
*Attorney, Agent, or Firm*—Antonelli, Terry, Stout & Kraus

[57] ABSTRACT

A nutrient composition such as infusions and nutrient preparations, which contains β-alanyl-L-glutamine.

6 Claims, No Drawings

NUTRIENT COMPOSITION

This application is a 371 of PCT/JP94/00101 filed Jan. 26, 1994.

TECHNICAL FIELD

The present invention relates to β-alanyl-L-glutamine-containing nutrient compositions such as infusions and nutrient preparations.

PRIOR ART

As a means for supplementing nutrients to mammals including humans, it is known to supplement amino acids singly or in combination with proteins, vitamins and the like orally or through injection. For example, L-glutamine must be supplemented to a patient in postoperative catabolic condition since the quantity of L-glutamine in the muscle of such a patient seriously decreases. However, because of its heat instability in solution, L-glutamine itself cannot be contained in a nutrient composition which should be sterilized by heating.

It is known L-glutamine, which is thermally unstable in solution, is supplied in the form of a nutrient composition for mammals by converting L-glutamine into a dipeptide. For example, there are known a nutrient composition containing L-alanyl-L-glutamine (DE3206784A), a nutrient composition containing glycyl-L-glutamine (JPA-61-247354), a nutrient composition containing L-aspartyl-L-glutamine (JPA-62-151156), and a nutrient composition containing L-glutamyl-L-glutamine (WO90/11024, U.S. Pat. No. 5,134,125).

In the nutrient compositions containing dipeptides of L-glutamine such as L-alanyl-L-glutamine, glycyl-L-glutamine, L-aspartyl-L-glutamine and L-glutamyl-L-glutamine, heat stability is improved in comparison with L-glutamine. Still, under sterilizing conditions, the depeptides are not satisfactory in heat stability, and therefore, it has been desired to be developed an L-glutamine-containing substance which is superior in heat stability.

DISCLOSURE OF THE INVENTION

The present invention relates to β-alanyl-L-glutamine-containing nutrient compositions having improved solubility in water and excellent heat stability.

Examples of nutrient compositions include amino acid infusions and nutrient preparations.

Amino acid infusions of the present invention contain β-alanyl-L-glutamine, and at least one of essential amino acids such as glycine and L-isomers of isoleucine, leucine, lysine, phenylalanine, methionine, threonine, tryptophane, valine, arginine, histidine, alanine, aspartic acid, cysteine, glutamic acid, proline, serine and tyrosine and salts of those essential amino acids. If necessary, the amino acid infusions may additionally contain carbohydrates such as glucose, fructose, xylitol, sorbitol and maltose, polyhydric alcohols such as glycerol, lipids such as soy bean oil, cotton seed oil, sesame oil, yolk lecithin and soy bean lecithin, vitamins such as vitamin A, vitamin B1, vitamin B2, vitamin B6, nicotinic acid, pantothenic acid, vitamin C, vitamin D, vitamin E, biotin and folic acid, electrolytes such as sodium chloride, sodium acetate, potassium chloride, magnesium sulfate, magnecium chloride, calcium chloride, dipotassium hydrogenphosphate and sodium dihydrogenphosphate, halogens such as iodine, and metals such as iron, zinc, manganese, copper and cobalt.

β-Alanyl-L-glutamine used in the present invention is a known compound, and it can be synthesized according to a known process described, e.g., in CA, Vol.70, 38090n(1969).

An amino acid infusion can be obtained in the following manner: (a) To β-alanyl-L-glutamine and at least one of the above-mentioned amino acids and additives is added 33 to 10,000 times as much distilled water for injection or aqueous solution such as physiological saline solution as β-alanyl-L-glutamine by weight, followed by thorough stirring to completely dissolve solids; or (b) To a solution containing at least one of the above-mentioned amino acids is added 0.001 to 30 wt % of β-alanyl-L-glutamine, followed by dissolving. The dissolving of β-alanyl-L-glutamine and amino acids can be carried out, if necessary, with heating at 25° to 50° C. The pH of the obtained solution is adjusted at 4.0 to 7.5 with acetic acid, hydrochloric acid, lactic acid, malic acid, citric acid, succinic acid, fumaric acid, sodium hydroxide, and the like. The resulting solution is then subjected to a sterilizing treatment such as heat sterilization or sterilizing filtration to obtain an amino acid infusion. Generally, an amino acid infusion is administered intravenously.

Table 1 shows an example of composition of an amino acid infusion of the present invention.

TABLE 1

| Composition | (mg/dl) |
| --- | --- |
| L-Isoleucine | 160–1600 |
| L-Leucine | 180–2000 |
| L-Lysine hydrochloride | 180–2400 |
| L-Phenylalanine | 130–1400 |
| L-Methionine | 50–1200 |
| L-Threonine | 80–720 |
| L-Tryptophane | 30–350 |
| L-Valine | 70–1600 |
| L-Arginine hydrochloride | 120–2500 |
| L-Histidine hydrochloride | 50–900 |
| Glycine | 0–2500 |
| L-Alanine | 0–2000 |
| Sodium L-Aspartate | 0–1300 |
| L-Cysteine | 0–200 |
| Sodium L-glutamate | 0–1300 |
| β-alanyl-L-glutamine | 1–20000 |
| L-Proline | 0–1080 |
| L-Serine | 0–1200 |
| L-Tyrosine | 0–90 |

The nutrient preparation of the present invention is used mainly as nutrient compositions for oral or enteral administration. In case of oral administration, it is preferred to mix water, proteins, carbohydrates, lipids, vitamins, minerals, pseudo-tasting agents, sweeteners, flavoring agents, dyes, and the like.

Examples of proteins include casein, hydrolyzed products thereof, gelatin, skim milk and powder of egg yolk. Example of carbohydrates include starch, dextrin, cyclodextrin, glucose, reduced maltose, lactose and malt extracts. Examples of lipids include middle chain fatty acids and yolk oil. Examples of vitamins include vitamin A, thiamine, riboflavin, pyridoxin, niacin, pantothenic acid, cyanocobalamin, L-ascorbic acid and α-tocopherol. Examples of minerals include sodium chloride, potassium chloride, calcium chloride and iron lactate. Examples of minerals include sodium chloride, potassium chloride, calcium chloride and iron lactate. Examples of pseudo-tasting agents include inosinic acid. Examples of sweeteners include aspartame, D-xylose and D-sorbitol. Examples of flavoring agents include citric acid and orange flavors. Examples of dyes include β-carotene and copper chlorophyll.

The nutrient preparations of the present invention can be obtained by adding to 1 liter of water at least 0.02 to 500 g (0.002 to 50% by weight), preferably 1 to 300 g (0.1 to 30% by weight) of proteins, 0.02 to 800 g (0.002 to 80% by weight), preferably 1 to 500 g (0.1 to 50% by weight) of carbohydrates and 0.01 to 300 g (0.001 to 30% by weight), preferably 1 to 150 g (0.1 to 15% by weight) of β-alanyl-L-glutamine, followed by stirring and dissolving, if necessary with heating at 40° to 120° C. The nutrient preparation can be sealed in a water-proof bag, bottle, can, etc. in the state of liquid or jelly and then thermally sterilized. Alternatively, the thermally sterilized liquid nutrient preparation itself can be dried by freeze-drying or the like and stored in a dry state, which can be used by dissolving in water, etc., just before use.

The heat stability and solubility of β-alanyl-L-glutamine will be shown in the following test examples.

TEST EXAMPLE 1

Each of aqueous 10 mM solutions of β-alanyl-L-glutamine, L-alanyl-L-glutamine (control) and L-glutamine (control) adjusted at pH 6.5 with sodium hydroxide was heated in an autoclave at 120° C. for a period of 20 minutes or 120 minutes. The residual rate of each of the compounds after heating was determined. The result is shown in Table 2.

TABLE 2

|  | Residual Rate after Heat Sterilization | |
| --- | --- | --- |
|  | 20 min. | 120 min. |
| β-Alanyl-L-glutamine | 100% | 99% |
| L-Alanyl-L-glutamine | 98% | 91% |
| L-Glutamine | 9% | 0% |

Table 2 shows that when the solutions were heated for 20 minutes, β-alanyl-L-glutamine remained entirely without being decomposed, whereas the control sample of L-alanyl-L-glutamine was partly decomposed and about 90% of L-glutamine was decomposed. Furthermore, when the solutions were heated for 120 minutes, L-glutamine was decomposed completely, and 99% of β-alanyl-L-glutamine remained, the residual rate of which is higher than that of L-alanyl-L-glutamine.

TEST EXAMPLE 2

Each of β-alanyl-L-glutamine, L-alanyl-L-glutamine (control) and L-glutamine (control) was dissolved into 1 liter of water (25° C.). Each of their maximum amounts dissolved in the water was determined. The result is shown in Table 3.

TABLE 3

|  | Amount Dissolved in 1 liter of Water (g) |
| --- | --- |
| β-Alanyl-L-glutamine | 952 |
| L-Alanyl-L-glutamine | 599 |
| L-Glutamine | 43 |

Table 3 shows that β-alanyl-L-glutamine has the highest solubility.

BEST MODE FOR CARRYING OUT THE INVENTION

Examples are shown below.

EXAMPLE 1

One liter of distilled water for injection at about 70° C. was added to dissolve a mixture of the amino acid composition shown in Table 4 and 10 g of β-alanyl-L-glutamine. The pH was adjusted at 6.5 with sodium hydroxide solution. The solution was filtered through a millipore filter (0.45 μm). The filtrate was packed in glass bottles in 200 ml portions, followed by blowing with aseptic nitrogen gas for 30 seconds. After sealing, the glass bottles were sterilized by heating at 120° C. for 20 minutes to prepare amino acid infusions.

TABLE 4

| L-Isoleucine | 4.6 g |
| --- | --- |
| L-Leucine | 7.7 g |
| L-Lysine hydrochloride | 5.0 g |
| L-Phenylalanine | 4.3 g |
| L-Methionine | 2.1 g |
| L-Threonine | 2.9 g |
| L-Tryptophane | 1.0 g |
| L-Valine | 4.9 g |
| L-Arginine hydrochloride | 6.1 g |
| L-Histidine hydrochloride | 2.6 g |
| Glycine | 3.4 g |
| L-Alanine | 4.6 g |
| Sodium L-Aspartate | 0.3 g |
| L-Cysteine | 0.3 g |
| Sodium L-glutamate | 0.3 g |
| L-Proline | 3.9 g |
| L-Serine | 2.3 g |
| L-Tyrosine | 0.3 g |

EXAMPLE 2

To 500 ml of water were added 10 g of casein hydrolysate, 2.5 g of β-alanyl-L-glutamine, 6.3 g of cyclodextrin, 0.11 g of inosinic acid, 16 g of citric acid and 6.8 g of reduced maltose. Then, 0.07 ml of orange flavor was added thereto. The resulting solution was sterilized by heating at 120° C. for 20 minutes to prepare a nutrient preparation for oral nutrient supplementation.

EXAMPLE 3

To 10 g of casein hydrolysate, 8 g of gelatin, 2.5 g of β-alanyl-L-glutamine, 20 g of dextrin and 20 g of reduced maltose was added 300 ml of water, and the mixture was heated at 100° C. for 30 minutes. The solution was then cooled to prepare a jelly-like nutrient preparation.

INDUSTRIAL APPLICABILITY

The β-alanyl-L-glutamine-containing nutrient compositions of the present invention are useful as infusions and nutrient preparations.

We claim:

1. A nutrient composition containing β-alanyl-L-glutamine.

2. A nutrient composition according to claim 1, wherein said composition contains β-alanyl-L-glutamine in an amount of 0.001 to 30% by weight.

3. A nutrient composition according to claim 1, wherein said composition is a composition for mammals.

4. A nutrient composition according to claim 1, wherein said nutrient composition is an amino acid infusion or a nutrient preparation.

5. A nutrient composition according to claim 4, wherein said amino acid infusion has the following composition:

| | |
|---|---|
| L-Isoleucine | 160–1600 (mg/dl) |
| L-Leucine | 180–2000 |
| L-Lysine hydrochloride | 180–2400 |
| L-Phenylalanine | 130–1400 |
| L-Methionine | 50–1200 |
| L-Threonine | 80–720 |
| L-Tryptophane | 30–350 |
| L-Valine | 70–1600 |
| L-Arginine hydrochloride | 120–2500 |
| L-Histidine hydrochloride | 50–900 |
| Glycine | 0–2500 |
| L-Alanine | 0–2000 |

-continued

| | |
|---|---|
| Sodium L-Aspartate | 0–1300 |
| L-Cysteine | 0–200 |
| Sodium L-glutamate | 0–1300 |
| β-alanyl-L-glutamine | 1–20000 |
| L-Proline | 0–1080 |
| L-Serine | 0–1200 |
| L-Tyrosine | 0–90 |

6. A nutrient composition according to claim 4, wherein said nutrient preparation contains at least 0.002 to 50% by weight of proteins, 0.002 to 80% by weight of carbohydrates and 0.001 to 30% by weight of β-alanyl-L-glutamine.

* * * * *